(12) United States Patent
Huang et al.

(10) Patent No.: US 6,369,246 B2
(45) Date of Patent: Apr. 9, 2002

(54) SYNTHESIS AND PHARMACEUTICALS OF NOVEL 9-SUBSTITUTED-1,5-DICHLOROANTHRACENE ANALOGS

(75) Inventors: Hsu-Shan Huang; Kung-Yuan Lee; Chang-Hsin Shi; Hsien-Chin Hsu, all of Taipei (TW)

(73) Assignee: Dr. Keith Chan, GloboAsia, LLC, Hanover, MD (US)

( * ) Notice: Subject to any disclaimer, the term of this patent is extended or adjusted under 35 U.S.C. 154(b) by 0 days.

(21) Appl. No.: 09/797,965

(22) Filed: Mar. 5, 2001

Related U.S. Application Data

(63) Continuation-in-part of application No. 09/290,865, filed on Apr. 14, 1999, now abandoned.

(51) Int. Cl.[7] .......................... C07C 50/16; A61K 31/21
(52) U.S. Cl. ........................................ 552/290; 514/510
(58) Field of Search ........................... 552/290; 514/510

(56) References Cited

PUBLICATIONS

Cristol et al, J. Am. Chem. Soc., 1955, vol. 77, pp. 583, 588.*
Banett et al, Chem. Ber., 1925, vol. 58 p. 979.*

* cited by examiner

Primary Examiner—Alton Pryor
(74) Attorney, Agent, or Firm—Fei-Fei Chao; Venable, Baetjer, Howard & Civiletti, LLP

(57) ABSTRACT

The invention relates to novel anthracene compounds useful in the treatment of allergic, inflammatory conditions, tumor conditions and therapeutic compositions containing such compounds. The compounds of the present invention are 9-acyloxy-substituted 1,5-dichloroanthracene or analogs thereof. According to the practice of the invention, there are provided 9-acyloxy substituted 1,5-dichloroanthracene compounds according to formula III:

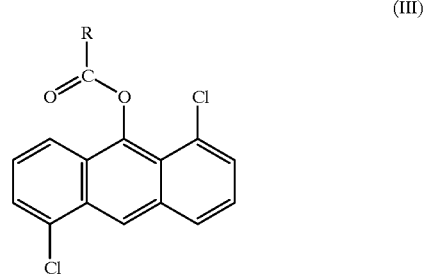

(III)

wherein R represents a straight or branched chain alkyl group having 1 to 6 carbons which may be substituted with one or more groups of $R_1$, or R represents phenyl or benzyl which may be substituted with one or two groups of $R_2$; wherein $R_1$ is selected from the group consisting of halogen, —$NO_2$, —$OCH_3$, $OCH_2CH_3$, and —$OCH_2CH_2CH_3$; and wherein $R_2$ is selected from the group consisting of a straight or branched chain alkyl group having 1 to 4 carbons, halogen, —$NO_2$, —$OCH_3$, —$OCH_2CH_3$, and —$OCH_2CH_2CH_3$.

28 Claims, 3 Drawing Sheets

(1) $R_1$=H; $R_2$= -NH-(CH$_2$)$_2$-NH-(CH$_2$)$_2$-OH (2) $R_1$=OH; $R_2$= -NH-(CH$_2$)$_2$-NH-(CH$_2$)$_2$-OH (a) SnCl$_2$, HCl, HOAC, 118°C
(b) ROCCl, pyridine, CH$_2$Cl$_2$ Perspective View of The Molecular Structure of Compound 3o.

SYNTHESIS AND PHARMACEUTICALS OF NOVEL 9-SUBSTITUTED-1,5-DICHLOROANTHRACENE ANALOGS

RELATED APPLICATION

This application is a continuation-in-part of U.S. patent application Ser. No. 09/290,865 now abdn, filed on Apr. 14, 1999, which is herein incorporated by reference.

BACKGROUND OF THE INVENTION

1. Field of the Invention

This invention relates to novel anthracene compounds useful in the treatment of allergic, inflammatory conditions, tumor conditions and therapeutic compositions containing such compounds. The invention relates also to the therapeutic compositions effective at low dose with low irritancy. These anthracene compounds possess antitumor, antiproliferative, antipsoriatic, antiinflammatory, or antioxidant activity.

2. Description of the Prior Art

The discovery of the antitumor activity of 1,4-bis [(aminoalkyl)amino]anthracene-9, 10-diones such as ametantrone (1) and mitoxantrone (2) (FIG. 1) (Zee-Cheng, R. K. V. et al., *J. Med. Chem.*, 21, 291–294 (1978); Zee-Cheng, R. K. V. et al., *J. Pharm. Sci.*, 71, 708–709 (1982); Murdock, K. C. et al., *J. Med. Chem.*, 22, 1024–1030 (1979)) has led to numerous physicochemical and pharmacological studies on the tumoricidal mechanisms of these chemotypes. Krapcho, A. P. et al., *J. Med. Chem.*, 341, 2373–2380 (1991); Morier-Teissier, E. et al., *J. Med. Chem.*, 36, 2084–2090 (1993). Additional references disclose 1,4- and 2,6-disubstituted or regioisomeric amidoanthracene-9,10-dione derivatives as inhibitors of human telomerase. Perry, P. J. et al., *J. Med. Chem.*, 41, 3253–3260 (1998) and Perry, P. J. et al., *J. Med. Chem.*, 41, 4873–4884 (1998).

Although the active mechanism of the antitumor activity of the anthracene-9,10-diones such as ametantrone (1) and mitoxantrone (2) is probably multimodal in nature, a number of studies have indicated that an intercalative interaction with DNA may be a major cellular event. Denny, W. A., *Anti-Cancer Drug Design*, 4, 241–263 (1989). Antitumor quinones represent the second largest class of clinically approved anticancer agents in the U.S.A., second only to the chloroethyl alkylating agents. They have been selected from the large number of naturally occurring quinones (Moore, H. W et al., *Drugs Expl. Clin. Res.*, 12, 475–494, (1986)) and from synthetic quinones. Bruce, J. M. ed., *Benzoquinones and Related Compounds*, Vol. 3, Part 4, 1–306, (1974). The planar tricyclic system is known to intercalate into DNA base pairs and interfere in the transcription and replication processes of the cell. Johnson, R. K. et al., *Cancer Treat. Rep.*, 63, 425–439 (1979); Lown, J. W. et al., *Biochemisty*, 24, 4028–4035 (1985). The DNA binding affinity (quantified as a binding affinity constant) and the dissociation rate constant for the DNA-ligand complex have been evaluated. Drug-DNA binding constants for ametantrone (1), mitoxantrone (2) and related congeners with calf thymus DNA show a large sensitivity to the position and number of the OH substitutions and the nature of the charged side chain. Denny, W A., *Anti-Cancer Drug Design*, 4, 241–263 (1989).

Normal human cells undergo a finite number of cell divisions and ultimately enter a nondividing state called replicative senescence. During successive rounds of cell division, the end-replication problem results in telomere shortening and ultimately senescence. As such, the loss of telomeric repeats after each round of cell division has been likened to a "biological clock" limiting the proliferative life span of normal somatic cells. Harley, C. B. et al., *Nature*, 345, 458–460 (1990). Consequently, telomerase has been proposed as a potentially highly selective target for the development of a novel class of antiproliferative agents. However, in order for a therapeutic treatment to be effective, both the inflammatory and hyperproliferative aspects of the condition must be addressed. Substantial evidence suggests that free radicals and active oxygen species play a key role in both the therapeutic activity and side effects of anthracenone derivatives.

Anthraquinone-based compounds currently occupy a prominent position in cancer chemotherapy, with the naturally occurring aminoglycoside anthracycline doxorubicin and the aminoanthraquinone mitoxantrone both being in clinical use. These 1,5-dichloro-9(10H)-anthracenone compounds contain alkylacyl or arylacyl moieties at the C-9 position resulting in enhanced antiproliferative activity of the compounds. These blocked compounds may be further modified by introducing the phenolic form of the arylacyl or alkylacyl substituent.

As noted above, cancer is typically characterized by hyperproliferative component. There is thus a continuing need for effective compounds that address these aspects of cancer disease.

SUMMARY OF THE INVENTION

The present invention is directed to novel 9-substituted-1,5-dichloroanthracene compounds and salts thereof having therapeutic utility with respect to allergic or inflammatory or tumor conditions. In particular, many of the improved anthracene compounds provided for according to the invention are effective at low concentrations for the treatment of patients suffering from allergic or inflammatory or tumor conditions. Because these compounds may be administered at low concentrations, the undesirable allergic or inflammatory effects caused in whole or in part by free radicals or active oxygen species that are generated by anthracenone compounds are substantially eliminated.

Accordingly, in one embodiment of the invention, there is provided an anthracene compound according to Formula III below, said compound containing a substituent R, wherein R represents a branched or straight chain alkyl group having from 1 to 4 carbon atoms, said alkyl group being substituted with at least one substituent selected from carboxyl, carboxyl ester, hydroxy, phenyl, benzyl, substituted benzyl and substituted phenyl groups.

In a preferred embodiment of the invention, R represents a substituted phenyl group having at least one substituent selected from methyl, halogen and nitro groups. In another preferred embodiment, R represents a straight or branched chain alkyl group having 1 to 4 carbon atoms, which may contain a substituent selected from acyl and phenyl groups. Additionally, there are provided compounds which are functional analogs of the compounds of Formula III.

As aforementioned, therapeutic compositions of the invention are effective at dosages that substantially eliminate the adverse inflammatory or irritancy effects associated with the use of anthracenone and related compounds. Accordingly, there is provided a therapeutic composition comprising a therapeutically effective amount of at least one compound of the invention and a pharmaceutically acceptable carrier. These compounds of the invention have antiproliferative effects and antineoplastic effects.

Further additional representative and preferred aspects of the invention are described below according to the following detailed description of the invention.

DETAILED DESCRIPTION OF THE INVENTION

As set forth above, the compounds of the invention are 9-acyloxy-1,5-dichloroanthracene analogs. According to of the invention, there are provided 9-substituted-1,5-dichloroanthracene compounds according to Formula III.

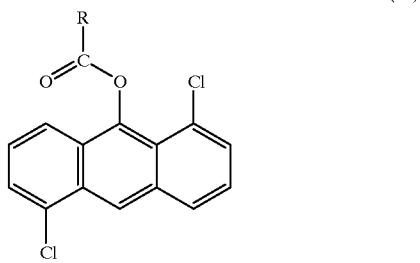

(III)

wherein R represents a straight or branched chain alkyl group having 1 to 6 carbon atoms, phenyl or benzyl, wherein the alkyl group may be substituted with one or more groups $R_1$ and the phenyl or benzyl group may be substituted with one or two groups $R_2$. $R_1$ is a group selected from halogen, $NO_2$, $CH_3O$, $CH_3CH_2O$, and $CH_3CH_2CH_2O$. $R_2$ is a group selected from a straight or branched chain alkyl group having 1 to 4 carbon atoms, halogen, $NO_2$, $CH_3O$, $CH_3$, $CH_2O$, $CH_3CH_2CH_2O$.

In preferred compounds according to the invention, R represents a straight or branched chain alkyl group having 1 to 4 carbon atoms which may be substituted with one or more groups $R_1$, selected from Cl, $NO_2$, $CH_3O$. In other preferred embodiments, R is a phenyl or benzyl group having one or two substituents $R_2$, selected from a straight or branched chain alkyl group having 1 to 4 carbon atoms, Cl, $NO_2$, $CH_3O$. Suitable compounds of the invention described in Table 1 (infra).

Figure 1:
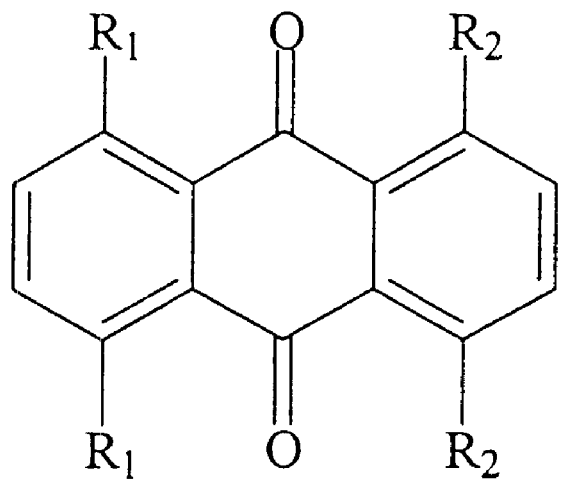
FIG. 1 Shows the structure of prior art anthraquinonic derivatives.
Figure 2:
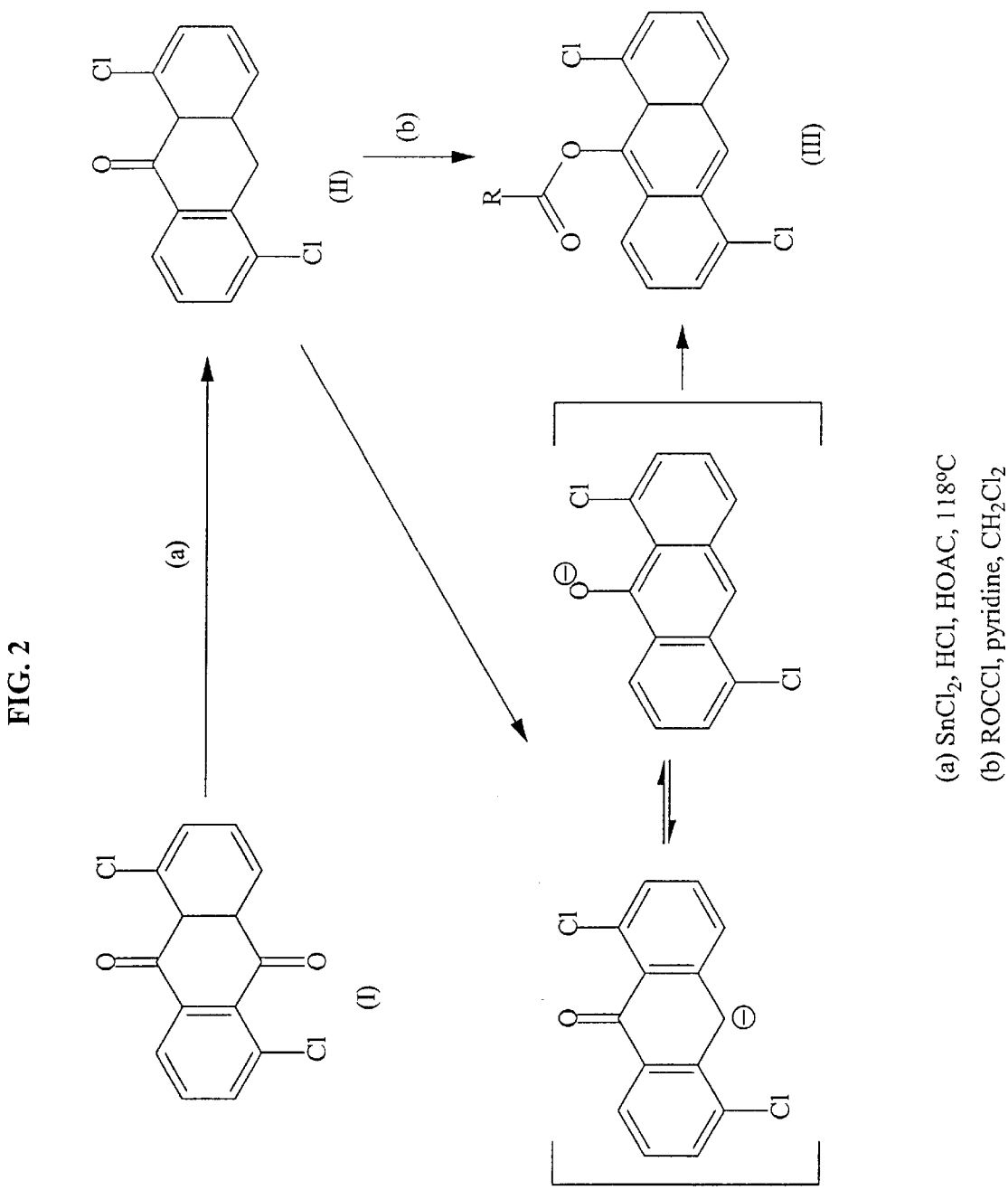
FIG. 2 is an outline of the synthesis of the 9-substituted-1,5-dichloroanthracene compounds.

In the course of synthesis of the 9-substituted-1,5-dichloroanthracenes, it was found that the molecule reacted to the acylating agents in an unusual manner. Introduction of the 9-acyloxy functionality onto the anthracene nucleus (compounds 3a—w) was achieved by reaction of the appropriate acyl chlorides with 1,5-dichloroanthrone under weakly basic conditions, e.g. pyridine, where ester formation takes place at the C-9 oxygen via the enol tautomer (FIG. 2).

For the pharmaceutical compositions according to the invention, salts of 9-substituted-1,5-dichloroanthracene compounds are in particular salts with the pharmaceutically acceptable base. Excipients such as magnesium stearate, corn starch, starch, lactose, sodium hydroxymethylcellulose, ethanol, glycerol etc. may be added in the preparation of pharmaceutical compositions containing 1,5-dichloro-9-acyloxyanthracene derivatives of the present invention. The pharmaceutical compositions of the invention may be in an injectable form or formulated into tablet, pill or other solid preparation forms. The pH value for injectable forms may be adjusted with phosphate buffer. Generally, dosage used for injectable forms is 25–100 mg. For solid preparations, an effective dosage is 3–500 mg, administered 2 to 3 times a day.

Clinical Indications Subject to Treatment

The following conditions are selected for description herein as being representative of inflammatory, allergic, antioxidant, or neoplastic conditions that are suitable for treatment according to the practice of the invention. Each of these conditions involves intimation hyperproliferation and/or generation of free radicals and active oxygen species.

Neoplastic Conditions

The therapeutic compositions of the invention may be used in the treatment of a wide variety of cancers such as carcinomas, sarcomas, melanomas and lymphomas, which may affect a wide variety of organs, including, for example, the lungs, mammary tissue, prostate gland, small or large intestine, liver, heart, skin, pancreas and brain. The therapeutic compositions may be administered by injection (intravenously, intralesionally, peritoneally, subcutaneously), or by topical application and the like as would be suggested according to the routine practice of the art.

Psoriasis and Contact Dermatitis

Psoriasis is a widespread, chronic, inflammatory and scaling skin disease. Contact dermatitis, in contrast, is a short term allergic condition characterized by scaling skin. Both psoriasis and contact dermatitis are characterized by increased epidermal cell proliferation at the affected site or sites, i.e. lesions. Muller, K., et al., *J. Med. Chem.*, 39, 3132–3138 (1996).

Arthritic Disease

Rheumatoid arthritis is a chronic inflammatory disease, primarily of the joints, that may result in permanent loss of joint function. Irreversible loss of joint function is attributed to severe degradation of collagen, bone, ligament and tendon. Associated chronic intimation results, in part, from immune response at the affected joint, although the exact nature of the triggering antigens is unknown. The immune response may be autoimmune in origin. Mullins, D. E. and Rohrlich, S. T., *Biochemica et Biophysica Acta*, 695, 177–214 (1983). The etiology has been described is in detail. (pp. 192–193.) Briefly, there is a progressive loss of cartilage (a connective tissue) caused by invading cells. Both collagen and proteoglycan components of the cartilage are degraded by enzymes released at the affected site.

Therapeutic Compositions and Administration Thereof

The amount of 9-substituted-1,5-dichloroanthracene (or salt thereof) administered for the prevention or inhibition of an inflammatory or allergic condition, for antiproliferative or antineoplastic effect, can be determined readily for any particular patient according to recognized procedures. Additional information useful in the selection of therapeutic compositions is provided as follows. For use in the treatment of inflammatory or degenerative conditions, as those term are recognized in the art, the therapeutic compositions may be administered, for example, by injection at the affected site, by aerosol inhalation (as in the case of emphysema or pneumonia), or by topical application or transdermal absorption as would also be suggested according to the routine practice of the art.

As described above, the 9-substituted-1,5-dichloroanthracene (or salt thereof) may be incorporated into a pharmaceutically acceptable carrier or carriers for application (directly or indirectly) to the affected area. The nature of the carrier may vary widely and will depend on the intended location of application and other factors well known in the art. Such carriers of anthralin or anthracenone compounds are well known in the art. See, for example, Kammerau, B. et al., *J. Investigative Dermatology*, 64, 145–149 (1975).

Preparation of the Compounds of the Invention

FIG. 2 is an outline of a synthesis of the 9-substituted-1, 5-dichloroanthracene compounds (Formula III) according to the invention. As shown in FIG. 2, reduction of 1,5-dichloroanthraquinone (1) with $SnCl_2$ in boiling HCl and acetic acid proceeds with concomitant ether cleavage and leads to the corresponding 1,5-dichloro-9(10H)-anthracenone (II). In the course of synthesis of the 9-substituted-1,5-dichloroanthracene, it was found that the molecule reacted to the acylating agents in an unusual manner. Introduction of the 9-acyloxy functionality onto the anthracene nucleus (compounds 3a–w) was achieved by reaction of the appropriate acyl chlorides with 1,5-dichloro-9(10H)-anthrone under weakly basic conditions (pyridine), resulting in ester formation at the C-9 position via the enol tautomer (FIG. 2). When the anthrone was allowed to react with acyl chlorides in $CH_2Cl_2$ in the presence of a catalytic amount of pyridine, the reaction time is reduced compared to the noncatalyzed reaction. Specific methods for the preparation of several compounds according to the present invention are described below in Example 1. The structure of each of the synthesized compounds is confirmed by $^1$H-NMR spectrometry, mass spectrometry and elemental analysis as shown in Example 2. Procedures adapted from the descriptions and the following non-limiting examples will allow one skilled in the art to prepared similar compounds of the invention.

EXAMPLES

The following non-limiting examples are representative of the practice of the invention.

Example 1

Methods of Synthesis

The novel 9-substituted-1,5-dichloroanthracene compounds described in Table 1 were produced as follows.

1,5-dichloroanthraquinone (1) was reduced with $SnCl_2$ in boiling HCl and acetic acid with ether cleavage to give the corresponding 1,5 dichloro-9(10H)-anthracenone (II). To a solution of 1,5-dichloro-9(10H)anthracenone (1 mmol) and 0. 1 mL of pyridine in dry $CH_2Cl_2$ (20 mL) was added dropwise a solution of an appropriate acyl chloride (3 mmol) in dry $CH_2Cl_2$ (10 mL) under $N_2$. The reaction mixture was stirred at room temperature or refluxed for several hours. The solvent was removed and the residue purified by recrystallization and chromatography. This procedure was used to synthesize each of the compounds in Table 1.

Example 2

Structural Confirmation

All temperatures are reported in degrees centigrade. Melting points were determined with a Büchi 530 melting point apparatus and are uncorrected. Chromatography refers to column chromatography using silica gel (E. Merck, 70–230 mesh). $^1$H-NMR spectra were recorded with a Varian GEMR-H-300 (300 MHz); δ values are in ppm relative to a tetramethylsilane internal standard. Fourier-transform IR spectra (KBr) were recorded on a Perkin-Elmer 983G spectrometer. Mass spectra (EI, 70 eV, unless otherwise stated) were obtained on a Finnigan MAT TSQ-46 and Finnigan MAT TSQ-700. UV spectra were recorded on a Shimadzu UV-160.

(1) 1,5-Dichloro-9-acetyloxy-anthracene (3a)

The compound was synthesized as in Example 1 and analyzed by $^1$H-NMR (500 MHz $CDCl_3$), δ (ppm): 8.79 (H, s, H-10), 8.01 (H, d, J=8.4 Hz, H-2), 7.90 (H, d, J=8.8,H6), 7.62–7.58 (2H, m, H-4,8), 7.43–7.34 (2H, m, H-3,7), 2.60 (3H, s, $COCH_3$); $^{13}$C-NMR: (75 MHz, $CDCl_3$), δ (ppm): 170.58, 142.00, 134.51, 132.31, 130.54, 129.87, 129.61, 128.37, 126.97, 126.93, 126.80, 125.97, 123.81, 121.79, 121.67, 22. 1; MS m/z 304 (7), 262 (100); Anal. ($Cl_{16}H_{10}O_2Cl_2$); C, H.

(2) 1,5-Dichloro-9-benzoyloxy-anthracene (3L)

The compound was synthesized as in Example 1 and analyzed by $^1$H-NMR: (500 MHz, $CDCl_3$), δ (ppm): 8.82 (H, s, H-10), 8.40 (2H, d, J=8.1 Hz, H-2',6'), 8.01 (2H, d, J=8.4 Hz, H-2), 7.91 (H, d, J=8.8 Hz, H-6), 7.71 (H, t, J 7.5 Hz, H-4'), 7.61–7.58 (2H, m, H-4,8), 7.56–7.52 (2H, d, J=7.2 Hz, H-3',5'), 7.37-7.33 (2H, m, H-3,7); $^{13}$C-NMR: (75 MHz, $CDCl_3$), δ (ppm): 166.62, 142.41, 134.49, 132.64, 131.28, 130.43, 130.11, 129.98, 129.53, 129.40, 128.65, 127.24, 126.98, 126.00, 125.84, 122.45, 121.81; MS m/z 367 (10), 262 (7), 246 (4), 227 (5), 105 (100); Anal. ($C_{21}H_{12}O_2Cl_2$); C, H.

(3) 1,5-Dichloro-9-(m-toluyloxy)-anthracene (3n)

The compound was synthesized as in Example 1 and analyzed by $^1$H-NMR: (500 MHz, $CDCl_3$), δ (ppm): 8.74 (H, s, H-10), 8.15 (H, d, J=7.4 Hz, H-2',6'), 7.93 (H, d, J=8.8,H-2), 7.85 (H, dd, J=8.8, 0.9 Hz, H-6), 7.53–7.48 (2H, m, H-4,8), 7.46-7.39 (2H, m, H-4',5'), 7.29–7.25 (2H, m, H-3,7), 2.42 (3H, S, $COCH_3$); $^{13}$C-NMR: (75 MHz, $CDCl_3$), δ (ppm): 166.41, 142.98, 139.28, 135.31, 134.55, 132.58, 131.83, 130.40, 129.94, 129.90, 129.52, 129.31, 128.72, 128.55, 127.19, 126.94, 126.00, 123.79, 122.38,121.86, 21.97; MS m/z 381 (13), 119 (100); Anal. ($C_{22}H_{14}O_2Cl_2$); C, H.

(4) 1,5-Dichloro-9-(p-toluoxy)-anthracene (3o)

The compound was synthesized as in Example I and analyzed by $^1$H-NMR: (500 MHz, $CDCl_3$), δ (ppm): 8.81 (H, s, H-10), 8.28 (2H, d, J=8.1 Hz, H-2',6'), 8.01 (H, d, J=8.4 Hz, H-4), 7.91 (H, d, J=8.8,H-5'), 7.36–7.32 (2H, m, H-3,7), 2.58 (3H, s, $CH_3$); $^{13}$C-NMR: (75 MHz, $CDCl_3$), δ (ppm): 166.28, 145.43, 143.43, 134.56, 132.56, 131.43, 130.38, 130.13, 129.91, 129.51, 128.76, 127.28, 127.24, 126.97, 126.91, 125.99, 123.74, 122.49, 121.89, 22.44; MS m/z 380 (4), 119 (100); Anal. ($C_{22}H_{14}O_2Cl_2$); C, H.

Figure 3:
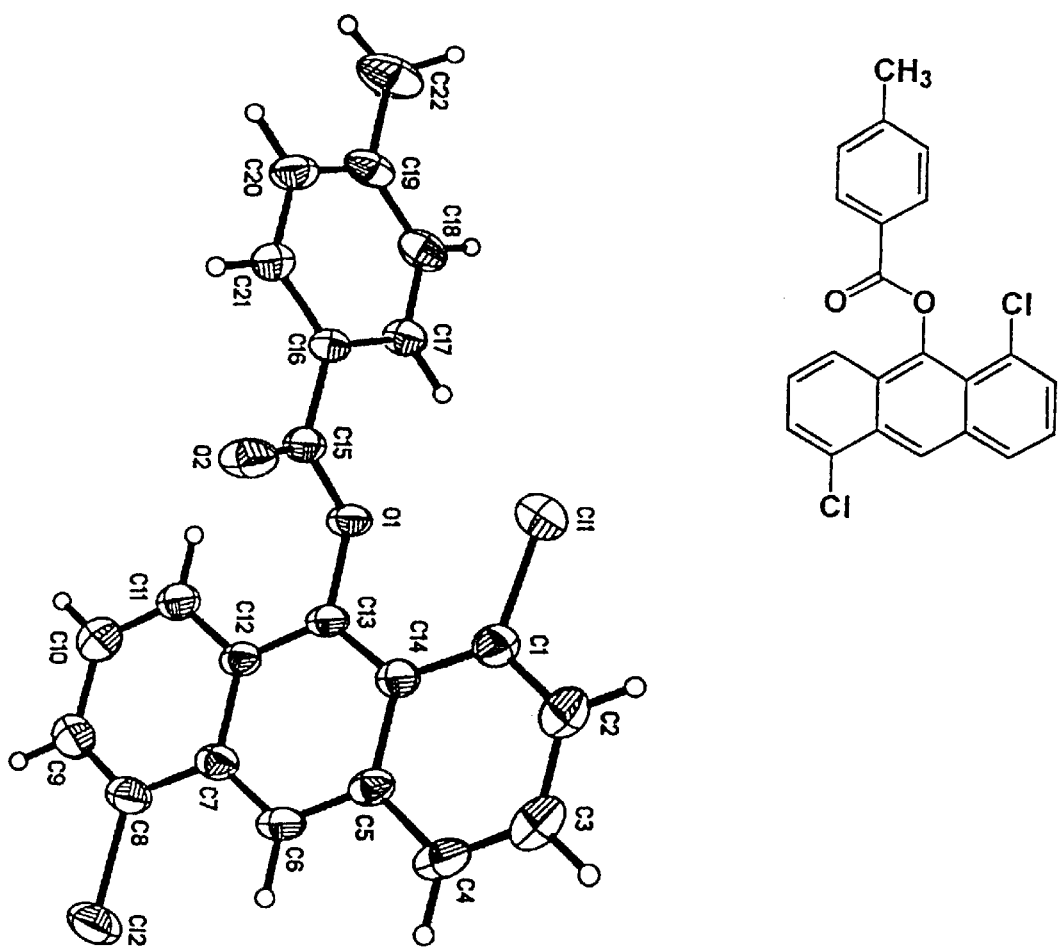
FIG. 3: Perspective view of the molecular structure of compound (3o).

The perspective view of the molecular structure of compound (3o) is shown in FIG. 3.

Example 3

Growth Inhibition Assay

Growth inhibition was measured in three human carcinoma cell lines (GBK KB and CHO) using a previously described in vivo assay. Hwang, J.-M. et al., *Chin. Med. J (Taipei)*, 51, 166–175 (1993). Human oral epidermoid carcinoma cells (KB cell line), human cervical carcinoma cells of ME 180 (GBM8401) and Chinese hamster ovary (CHO) cells grown in plateau phase were used in all experiments. Each cell line was further divided into control and experimental groups, respectively.

Stock solutions of the test compounds were prepared in DMSO and diluted with DMEM to give a final concentration of DMSO of 0.2%. Controls were performed with DMSO or with medium alone. The medium was removed and each well was rinsed with 100 μL PBS 48 hours after addition of the test compound to the culture. The cells were then incubated with sterile 0.5% trypsin, 0.2% EDTA in PBS for 20 minutes at 37° C. The detached cells from each well were suspended in DMEM and dispersed into single cells by gentle pipeting through an Eppendorf pipette and cell growth was determined directly by counting the cells in a Neubauer counting chamber using phase contrast microscopy. Inhibition was calculated by comparison of the mean values of the test compound (N=3) with the control (N=6–8) activity: (1-test compound/control) ×100. Inhibition was statistically significant compared to that of control (Student's t Test; P=0.05). $IC_{50}$ values (concentration required to inhibit cell growth by 50%) were determined for each agent which was derived by interpolation of a log inhibitor concentration versus response plot using four or more different concentrations of the compound spanning the 50% inhibition point.

Several compounds of the invention had an antiproliferative $IC_{50}$ value of less than 1.1 μM for GBM cell line. In particular, compounds 3g, 3j and A had $IC_{50}$ values of 1.4, 1.1 and 1.2 μM respectively. In addition, each of compounds 3j and 3v showed an $IC_{50}$ value of 11.0 μM and 12.6 μM in the KB assay. The results of this assay are provided in Table 1.

Example 4

Taq Polymerase Assay

Prior to the evaluation of compounds in the PCR-based telomerase assay, the agents were tested for their ability to inhibit Taq polymerase in order to address the selectivity of polymerase/telomerase inhibition. Compounds were included at both 10 and 50 μM final concentrations in a PCR 50 μL master mix comprising 10 ng of pCI-neo mammalian expression vector (Promega, Southampton, U.K.), forward (CGAGTTCCGCGT-TACATAAC) and reverse (GTCTGCTCGAAGCATTAACC) primers (200 nmol), reaction buffer (75 mM Tris-HCl, pH 8.81, 20 mM $(NH_4)_2SO_4$, 0.01% v/v Tween 20), 2.5 mM $MgCl_2$, 200 μM of each deoxynucleotide triphosphate, and thermostable DNA polymerase ("red hot", Advanced Biotechnologies, 1.25 units). A reaction mix containing water and no drug was used as a positive control, producing a product of approximately 1 kb. Amplification (30 cycles of 94° C. for 1 min, 55° C. for 1 min, and 72° C. for 2.5 min) were performed using a thermal cycler (Hybaid, U.K.). PCR products were then separated by electrophoresis on a 2% w/w agarose gel and visualized using ethidium bromide. The results of this assay are provided in Table 2.

Example 5

Lipid Peroxidation Assay

Rat brain homogenate was prepared from the brains of freshly killed Wistar rats and its peroxidation. In the presence of iron ions was measured by the thiobarbituric acid (TBA). Teng, C. M. et al., *Eur. J. Pharmacol.*, 303, 129–139 (1996). Tetramethoxypropane was used as a standard, and the results were expressed as nanomoles of malondialdehyde equivalents per milligram of protein of rat brain homogenates.

In brief, whole brain tissue, excluding the cerebellum, was washed and homogenized in 10 volumes of ice-cold Krebs buffer (10 mM N-2 hydroxyethyl-piperazine-N'-2-ethanesulfonic acid (Hepes), 10 mM glucose, 140 mM NaCl, 3.6 mM KCl, 1.5 mM $CaCl_2$, 1.4 mM $KH_2PO_4$, 0.7 mM $MgSO_4$, pH 7.4) using a glass Dounce homogenizer. The homogenate was centrifuged at low speed (1000×g) for 10 min, and the resulting supernatant (adjusted to 2 mg/mL) was used immediately in lipid. peroxidation assays.

The reaction mixture with test compounds or vehicle was incubated for 10 min, then stimulated by addition of ferrous ion (200 μM freshly prepared), and maintained at 37° C. for 30 min. The reactions were terminated by adding 10 μM of ice-cold trichloroacetic acid solution (4% (w/v) in 0.3 N HCl) and 200 μM, of thiobarbituric acid-reactive substance reagent (0.5% (w/v) thiobarbituric acid in 50% (v/v) acetic acid). After boiling for 15 min, the samples were cooled and extracted with n-butanol. The extent of lipid peroxidation was estimated as thiobarbituric acid-reactive substances and was read at 532 nm in a spectrophotometer (Shimadzu UV-160). The results of this assay are provided in Table 3.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope of the invention, it is intended that all subject matter contained in the above description, shown in the accompanying drawing, or defined in the appended claims, be interpreted as descriptive, illustrative, and non-limiting. Modifications and variations of the present invention are possible in light of the above teachings. It is therefore to be understood that within the scope of the appended claims, the invention may be practiced otherwise than as specifically described.

TABLE 1

In vitro cytotoxicity data for novel 1,5-dichloroanthracene compounds of the invention

| Comp'd No. | R group | Formula | MW | mp (° C.) | $IC_{50}(\mu M)$[a] GBM | KB | CHO |
|---|---|---|---|---|---|---|---|
| 3a | $CH_3$ | $C_{16}H_{10}O_2Cl_2$ | 305.16 | 164–166 | 48.1 | 472.8 | 114.5 |
| 3b | $CH_2Br$ | $C_{16}H_9O_2Cl_2Br$ | 384.06 | 180–181 | 19.2 | 136.0 | 1012.5 |
| 3c | $CH_2Cl$ | $C_{16}H_9O_2Cl_3$ | 339.60 | 181–182 | 105.6 | 527.5 | 1.2 |
| 3d | $CH_2CH_3$ | $C_{17}H_{12}O_2Cl_2$ | 319.18 | 134–135 | 17.2 | 470.8 | 1157.6 |
| 3e | $CH(CH_3)_2$ | $C_{18}H_{14}O_2Cl_2$ | 332.17 | 116–118 | 195.5 | 430.8 | 1314.2 |
| 3f | $CH(CH_3)Cl$ | $C_{17}H_{11}O_2Cl_3$ | 353.63 | 120–122 | 125.8 | 374.1 | 954.9 |
| 3g | $CHCl_2$ | $C_{16}H_8O_2Cl_4$ | 374.05 | 138–140 | 1.4 | 527.8 | 1277.9 |
| 3h | $(CH_2)_2CH_3$ | $C_{18}H_{14}O_2Cl_2$ | 333.21 | 132–134 | 572.2 | 544.3 | 0.1 |

TABLE 1-continued

In vitro cytotoxicity data for novel 1,5-dichloroanthracene compounds of the invention

| Comp'd No. | R group | Formula | MW | mp (° C.) | IC$_{50}$($\mu$M)[a] GBM | KB | CHO |
|---|---|---|---|---|---|---|---|
| 3i | (CH$_2$)$_3$Br | C$_{18}$H$_{13}$O$_2$BrCl$_2$ | 412.11 | 118–120 | 205.2 | 457.3 | 109.9 |
| 3j | (CH$_2$)$_3$Cl | C$_{18}$H$_{13}$O$_2$Cl$_3$ | 367.65 | 130–132 | 1.1 | 11.0 | 1171.3 |
| 3k | (CH$_2$)$_4$CH$_3$ | C$_{20}$H$_{18}$O$_2$Cl$_2$ | 361.26 | 120–121 | 1.2 | 316.8 | 55.1 |
| 3L | C$_6$H$_5$ | C$_{21}$H$_{12}$O$_2$Cl$_2$ | 367.23 | 166–168 | 226.3 | 813.2 | 1437.2 |
| 3m | 2-CH$_3$C$_6$H$_4$ | C$_{22}$H$_{14}$O$_2$Cl$_2$ | 381.26 | 162–164 | 107.9 | 1136.4 | 1513.3 |
| 3n | 3-CH$_3$C$_6$H$_4$ | C$_{22}$H$_{14}$O$_2$Cl$_2$ | 381.26 | 172–173 | 397.9 | 110.9 | 1199.2 |
| 3o | 4-CH$_3$C$_6$H$_4$ | C$_{22}$H$_{14}$O$_2$Cl$_2$ | 381.26 | 204–206 | 11.2 | 865.2 | 11639 |
| 3p | 3-ClC$_6$H$_4$ | C$_{21}$H$_{11}$O$_2$Cl$_3$ | 401.67 | 172–174 | 11.7 | 1050.6 | 19840 |
| 3q | 4-ClC$_6$H$_4$ | C$_{21}$H$_{11}$O$_2$Cl$_3$ | 401.67 | 169–171 | —[b] | —[b] | —[b] |
| 3r | 4-NO$_2$C$_6$H$_4$ | C$_{21}$H$_{11}$NO$_4$Cl$_2$ | 412.22 | 198–200 | —[b] | —[b] | —[b] |
| 3s | 3-NO$_2$C$_6$H$_4$ | C$_{21}$H$_{11}$NO$_4$Cl$_2$ | 412.22 | 216–218 | 11.1 | 836.6 | 1481.7 |
| 3t | 4-Cl 2-CH$_3$O—C$_6$H$_3$ | C$_{22}$H$_{13}$O$_3$Cl$_3$ | 431.70 | 195–196 | 10.8 | 818.1 | 114.5 |
| 3u | 2,4-Cl$_2$C$_6$H$_3$ | C$_{21}$H$_{10}$O$_2$Cl$_4$ | 436.12 | 190–192 | 87.7 | 107.5 | 1182.7 |
| 3v | CH$_2$C$_6$H$_5$ | C$_{22}$H$_{14}$O$_2$Cl$_2$ | 381.25 | 152–154 | 109.8 | 12.6 | 1186.7 |
| 3w | CH$_2$CH$_2$C$_6$H$_5$ | C$_{23}$H$_{16}$O$_2$Cl$_2$ | 395.28 | 126–128 | 1734.8 | 936.3 | 1164.7 |
| Doxorubicin | | | | | 598.9 | 420.5 | 498.8 |
| Mitomycin-C | | | | | 1896.3 | 11720 | 2122.5 |
| Methotrexate | | | | | 9286.2 | 47180 | 9141.5 |

[a]Concentration required to inhibit cell growth by 50% relative to controls.
[b]Not dissolved.

TABLE 2

Taq inhibition data for novel 1,5-dichloro-anthracenes

| Comp'd No. | R group | Taq Inhibition 1 mM | 0.1 mM | 0.01 mM |
|---|---|---|---|---|
| 3b | CH$_2$Br | + | + | + |
| 3c | CH$_2$Cl | − | − | − |
| 3d | CH$_2$CH$_3$ | + | + | + |
| 3g | CHCl$_2$ | + | + | + |
| 3h | (CH$_2$)$_2$CH$_3$ | + | + | + |
| 3i | (CH$_2$)$_3$Br | − | − | − |
| 3j | (CH$_2$)$_3$Cl | + | + | − |
| 3k | (CH$_2$)$_4$CH$_3$ | + | + | + |
| 3m | 2-CH$_3$C$_6$H$_4$ | + | − | − |
| 3n | 3-CH$_3$C$_6$H$_4$ | + | + | − |
| 3p | 3-ClC$_6$H$_4$ | + | − | − |
| 3q | 4-ClC$_6$H$_4$ | + | − | − |
| 3r | 3-NO$_2$C$_6$H$_4$ | − | − | − |
| 3s | 4-NO$_2$C$_6$H$_4$ | − | − | − |
| 3u | 2,4-Cl$_2$C$_6$H$_3$ | + | + | − |
| 3v | CH$_2$C$_6$H$_5$ | + | + | − |
| 3w | CH$_2$CH$_2$C$_6$H$_5$ | + | + | + |

TABLE 3

Inhibitory effects of novel 1,5-dichloro-anthracene compounds of the invention on iron-induced lipid peroxidation in rat brain homogenates

| Comp'd No. | R group | % Inhibition[a] (10 $\mu$M) | % Inhibition[a] (1 $\mu$M) |
|---|---|---|---|
| 3a | CH$_3$ | 34.4 | 25.5 |
| 3b | CH$_2$Br | 100 | 100 |
| 3c | CH$_2$Cl | 100 | 100 |
| 3d | CH$_2$CH$_3$ | 100 | 100 |
| 3e | CH(CH$_3$)$_2$ | 28.6 | 1.5 |
| 3f | CH(CH$_3$)Cl | 60.6 | 9.8 |
| 3g | CHCl$_2$ | 100 | 61.7 |
| 3h | (CH$_2$)$_2$CH$_3$ | 17.7 | 11.8 |
| 3i | (CH$_2$)$_3$Br | 100 | 38.1 |
| 3j | (CH$_2$)$_3$Cl | 29.0 | 10.0 |
| 3k | (CH$_2$)$_4$CH$_3$ | 17.2 | 12.2 |
| 3L | C$_6$H$_5$ | 14.0 | 4.6 |
| 3m | 2-CH$_3$C$_6$H$_4$ | 23.0 | 0 |
| 3n | 3-CH$_3$C$_6$H$_4$ | 22.4 | 10.9 |
| 3o | 4-CH$_3$C$_6$H$_4$ | 25.6 | 2.9 |
| 3p | 3-ClC$_6$H$_4$ | 30.6 | 8.6 |
| 3q | 4-ClC$_6$H$_4$ | —[b] | —[b] |
| 3r | 4-NO$_2$C$_6$H$_4$ | —[b] | —[b] |
| 3s | 3-NO$_2$C$_6$H$_4$ | 35.7 | 5.9 |
| 3t | 4-Cl, 2-CH$_3$O—C$_6$H$_3$ | 10.3 | 0 |
| 3u | 2,4-Cl$_2$C$_6$H$_3$ | 16.0 | 1.7 |
| 3v | CH$_2$C$_6$H$_5$ | 32.8 | 13.7 |
| 3w | CH$_2$CH$_2$C$_6$H$_5$ | 36.6 | 29.3 |
| (+)-a-Tocopherol | | 100 | 61.6 |

[a]Relative percentage of inhibition
[b]Not dissolved.

What is claimed is:
1. A pharmaceutical compound according to Formula III,

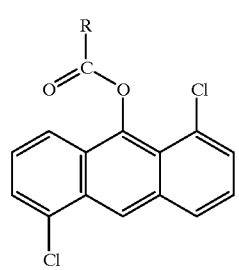

(III)

wherein R is selected from the group consisting of a straight or branched chain alkyl group having 1 to 6 carbons substituted with one or more R$_1$ groups, a benzyl group, a phenyl group which is substituted with one or two $R_2$ groups, and a benzyl group which is substituted with one or two $R_2$ groups;

wherein $R_1$ is selected from the group consisting of halogen, —$NO_2$, —$OCH_3$, $OCH_2CH_3$, and —$OCH_2CH_2CH_3$; and wherein $R_2$ is selected from the group consisting of a straight or branched chain alkyl group having 1 to 4 carbons, halogen, —$NO_2$, —$OCH_3$, —$OCH_2CH_3$, and —$OCH_2CH_2CH_3$.

2. The compound according to claim 1, wherein R represents a substituted phenyl group selected from the group consisting of 2—$CH_3C_6H_4$, 3—$CH_3C_6H_4$, 4—$CH_3C_6H_4$, 3—$ClC_6H_4$, 4—$ClC_6H_4$, 3—$NO_2C_6H_4$, 4—$NO_2C_6H_4$, 4—Cl—2—$CH_3OC_6H_3$, and 2,4—$Cl_2C_6H_3$.

3. The compound according to claim 1, wherein R represents a substituted alkyl group selected from the group consisting of $CH_2Br$, $CH_2Cl$, $CH(CH_3)Cl$, $CHCl_2$, $(CH_2)_3Br$, and $(CH_2)_3Cl$.

4. An anti-inflammatory drug, comprising, as an active ingredient, the pharmaceutical compound of claim 1.

5. An antioxidant, comprising, as an active ingredient, the pharmaceutical compound of claim 1.

6. An anti-dermatitis cancer drug, comprising, as an active ingredient, the pharmaceutical compound of claim 1.

7. A compound having the chemical structure of Formula III,

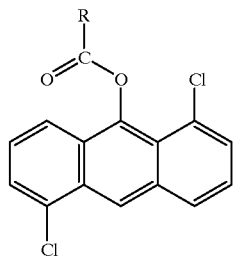

(III)

wherein R represents a phenyl or benzyl group having one or two substituents which is selected from the group of methyl, $NO_2$, $OCH_3$ and Cl.

8. A compound having the chemical structure of Formula III,

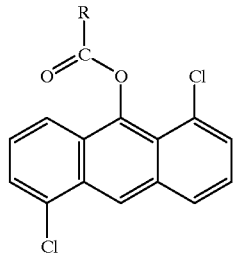

(III)

wherein R is $CH_2C_6H_5$ or $CH_2CH_2C_6H_5$.

9. A method for synthesis of 9-substituted-1,5-dichloroanthrecene compounds and salts thereof, comprising reacting 1,5-dichloroanthrone with an acyl chloride under weakly basic conditions to give the 9-subsituted-1,5-dichloroanthrancene according to Formula III

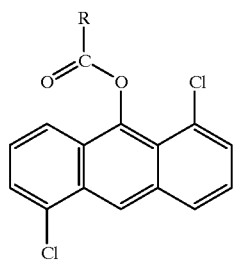

(III)

wherein R is selected from the group consisting of a straight chain alkyl group having 1 to 6 carbons which is optionally substituted with one or more $R_1$ groups, a branched chain alkyl group having 1 to 6 carbons which is optionally substituted with one or more $R_1$ groups, —$CH_2CH_2C_6H_5$, a phenyl which is substituted with one or more $R_2$ groups, and a benzyl group which is optionally substituted with one or two $R_2$ groups;

wherein $R_1$ is selected from the group consisting of halogen, —$NO_2$, —$OCH_3$, $OCH_2CH_3$, and —$OCH_2CH_2CH_3$; and wherein $R_2$ is selected from the group consisting of a straight or branched chain alkyl group having 1 to 4 carbons, halogen, —$NO_2$, —$OCH_3$, —$OCH_2CH_3$, and —$OCH_2CH_2CH_3$.

10. The method of claim 9 wherein the weakly basic condition is accomplished by the addition of pyridine.

11. A pharmaceutical compound which is synthesized by reacting 1,5-dichloroanthrone with an acyl chloride of the form RC(O)Cl under a weakly basic condition;

wherein R is selected from the group consisting of a straight chain alkyl group having 1 to 6 carbons which is substituted with one or more $R_1$ groups, a branched chain alkyl group having 1 to 6 carbons which is optionally substituted with one or more $R_1$ groups, —$CH_2CH_2C_6H_5$, a benzyl group, a phenyl group which is substituted with one or two groups $R_2$, and a benzyl group which is substituted with one or two groups $R_2$;

wherein $R_1$ is a group selected from halogen, —$NO_2$, —$OCH_3$, —$OCH_2CH_3$, and —$OCH_2CH_2CH_3$;

wherein $R_2$ is a group selected from a straight or branched chain alkyl group having 1 to 4 carbons, halogen, —$NO_2$, —$OCH_3$—$OCH_2CH_3$, and —$OCH_2CH_2CH_3$; and wherein said weakly basic condition is accomplished by the addition of pyridine.

12. The pharmaceutical compound according to claim 11, wherein the acyl chloride is benzoyl chloride or a substituted benzoyl chloride which is selected from the group consisting of 2-methylbenzoyl chloride, 3-methylbenzoyl chloride, 4-methylbenzoyl chloride, 3-chlorobenzoyl chloride, 4-chlorobenzoyl chloride, 3-nitrobenzoyl chloride, 4-nitrobenzoyl chloride, 4-chloro-2-methoxybenzoyl chloride and 2,4-dichlorobenzoyl chloride.

13. The pharmaceutical compound according to claim 11, wherein the acyl chloride is phenylacetyl chloride or a substituted phenylacetyl chloride having a substituent selected from the group consisting of methyl, nitro, methoxy and chloro.

14. The pharmaceutical compound according to claim 11, wherein the acyl chloride is bromoacetyl chloride, chloroacetyl chloride, propanoyl chloride, isobutyryl chloride, 2-chloropropanoyl chloride, dichloroacetyl chloride, butyryl chloride, 4-bromobutyrlyl chloride, 4-chlorobutyrlyl chloride, 3-phenylpropanoyl chloride or hexanoyl chloride.

15. The pharmaceutical compound according to claim 11, wherein the acyl chloride is benzoyl chloride and having a $^1$H-NMR characterized by signals at δ (ppm relative to tetramethyl silane) of approximately 8.82 (s), 8.40 (d), 8.01 (d), 7.91 (d), 7.71 (t), 7.61–7.58 (m), 7.56–7.52 (d), 7.37–7.33 (m), wherein s, d, t and m designate signals comprising a singlet, a doublet, a triplet, and a multiplet, respectively.

16. The pharmaceutical compound according to claim 11, wherein the acyl chloride is 3-methylbenzoyl chloride and having a $^1$H-NMR characterized by signals at δ (ppm relative to tetramethyl silane) of approximately 8.74 (s), 8.15 (d), 7.93 (d), 7.85 (dd), 7.53–7.48 (m), 7.46–7.39 (m), 7.29–7.25 (m), 2.42 (s) wherein s, d, dd and m designate signals comprising a singlet, a doublet, a doublet of doublets, and a multiplet, respectively.

17. A method for anti-cancer treatment, comprising administering a therapeutically effective amount of a pharmaceutical compound according to claim 11 or a pharmaceutically acceptable salt of said compound and optionally a pharmaceutical carrier to a patient in need of such treatment.

18. A method for treating abnormal proliferation, comprising administering a therapeutically effective amount of a pharmaceutical compound according to claim 11 or a pharmaceutically acceptable salt of said compound and optionally a pharmaceutical carrier to a patient in need of such treatment.

19. A method for enhancing an anti-oxidation affect, comprising administering a therapeutically effective amount of a pharmaceutical compound according to claim 11 or a pharmaceutically acceptable salt of said compound and optionally a pharmaceutical carrier to a patient in need of such treatment.

20. An anti-cancer drug, comprising, as an active ingredient, the pharmaceutical compound of claim 11.

21. An anti-inflammatory drug, comprising, as an active ingredient, the pharmaceutical compound of claim 11.

22. An antioxidant, comprising, as an active ingredient, the pharmaceutical compound of claim 11.

23. An anti-dermatitis cancer drug, comprising, as an active ingredient, the pharmaceutical compound of claim 11.

24. A method for inhibiting or treating an allergic or inflammatory condition, comprising administering a therapeutically effective amount of a pharmaceutical compound according to claim 11 or a pharmaceutically acceptable salt of said compound and optionally a pharmaceutical carrier to a patient in need of such treatment.

25. A method for inhibiting or treating an allergic or inflammatory condition, comprising administering to a patient a therapeutically effective amount of a pharmaceutical compound having the chemical structure of Formula III,

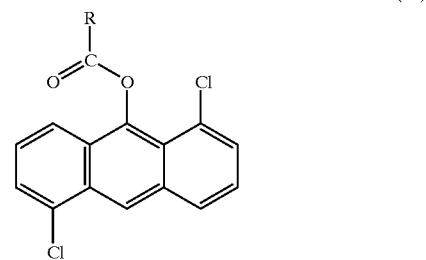

(III)

wherein R represents a straight or branched chain alkyl group having 1 to 6 carbons which may be substituted with one or more grous $R_1$, or R represents a a benzyl group, a phenyl group which may be substituted with one or two $R_2$ groups, and a benzyl group which is substituted with one or two $R_2$ groups;

wherein $R_1$ is selected from the group consisting of halogen, $-NO_2$, $-OCH_3$, $OCH_2CH_3$, and $-OCH_2CH_2CH_3$; and wherein $R_2$ is selected from the group consisting of a straight or branched chain alkyl group having 1 to 4 carbons, halogen, $-NO_2$, $-OCH_3$, $-OCH_2CH_3$, and $-OCH_2CH_2CH_3$.

26. A method for anti-cancer treatment, comprising administering a therapeutically effective amount of a pharmaceutical compound or a pharmaceutically acceptable salt of said compound and optionally a pharmaceutical carrier to a patient in need of such treatment, wherein said pharmaceutical compound has the chemical structure of Formula III according to claim 25.

27. A method for treating abnormal proliferation, comprising adminstering a therapeutically effective amount of a pharmaceutical compound or a pharmaceutically acceptable salt of said compound and optionally a pharmaceutical carrier to a patient in need of such treatment, wherein said pharmaceutical compound has the chemical structure of Formula III according to claim 25.

28. A method for enchancing an anti-oxidant effect, comprising adminstering a therapeutically effective amount of a pharmaceutical compound or a pharmaceutically acceptable salt of said compound and optionally a pharmaceutical carrier to a patient in need of such treatment, wherein said pharmaceutical compound has the chemical structure of Formula III according to claim 25.

* * * * *